United States Patent
Marra

(10) Patent No.: US 12,387,833 B2
(45) Date of Patent: Aug. 12, 2025

(54) APPARATUS FOR DIALYSIS AND COMMUNICATION METHOD FOR A DIALYSIS MACHINE

(71) Applicant: Bellco SRL, Mirandola (IT)

(72) Inventor: Antonio Giuseppe Marra, Bologna (IT)

(73) Assignee: Bellco S.R.L., Mirandola (IT)

( * ) Notice: Subject to any disclaimer, the term of this patent is extended or adjusted under 35 U.S.C. 154(b) by 0 days.

(21) Appl. No.: 17/509,673

(22) Filed: Oct. 25, 2021

(65) Prior Publication Data

US 2022/0130511 A1    Apr. 28, 2022

(30) Foreign Application Priority Data

Oct. 28, 2020 (EP) ..................................... 20204333

(51) Int. Cl.
*G16H 20/40*    (2018.01)
*G16H 40/67*    (2018.01)

(52) U.S. Cl.
CPC ............. *G16H 20/40* (2018.01); *G16H 40/67* (2018.01)

(58) Field of Classification Search
CPC ........ G16H 20/40; G16H 40/67; G16H 40/60; G16H 40/63; A61M 2205/3331; A61M 2205/3368; A61M 2205/3561; A61M 2205/50; A61M 1/28; A61M 1/284; A61M 1/287; F04B 49/065; H04W 4/80; H04W 76/15; H04W 88/06
See application file for complete search history.

(56) References Cited

U.S. PATENT DOCUMENTS

| | | |
|---|---|---|
| 5,324,422 A | 6/1994 | Colleran |
| 7,544,300 B2 | 6/2009 | Burbank |
| 7,749,393 B2 | 7/2010 | Brugger |
| 7,976,711 B2 | 7/2011 | Brugger |
| 8,202,420 B2 | 6/2012 | Brugger |
| 8,460,558 B2 | 6/2013 | Brugger |
| 8,585,634 B2 | 11/2013 | Neftel |
| 9,155,824 B2 | 10/2015 | Eyrard |
| 9,274,073 B2 | 3/2016 | Nier |
| 9,421,324 B2 * | 8/2016 | Sloan ................ A61M 5/14244 |
| 9,731,059 B2 | 8/2017 | Crnkovich |
| 9,861,733 B2 | 1/2018 | Burbank |

(Continued)

FOREIGN PATENT DOCUMENTS

| | | |
|---|---|---|
| EP | 0846470 A1 | 6/1998 |
| EP | 0655004 B1 | 6/1999 |

(Continued)

OTHER PUBLICATIONS

European Search Report for App. No. 20214462.2, dated Sep. 1, 2021.

(Continued)

*Primary Examiner* — Adnan Aziz

(57) ABSTRACT

A dialysis machine is provided with modules which are separated relative to the other. Communications links are established between the modules. In the event of interference and a drop in quality on one communications link communications are routed via the other communications link. The communications link may be over domestic wiring. A communications method is also described for use in such a medical machine.

14 Claims, 3 Drawing Sheets

(56) References Cited

U.S. PATENT DOCUMENTS

| | | | |
|---|---|---|---|
| 9,907,897 B2 | 3/2018 | Burbank et al. | |
| 10,076,599 B2 | 9/2018 | Eyrard | |
| 2008/0064328 A1* | 3/2008 | Wesel | H04B 7/195 455/13.3 |
| 2008/0097911 A1* | 4/2008 | Dicks | G16H 40/67 705/50 |
| 2009/0009290 A1* | 1/2009 | Kneip | A61M 1/155 340/10.1 |
| 2013/0003595 A1* | 1/2013 | Soomro | G16H 40/67 370/252 |
| 2014/0006510 A1* | 1/2014 | Hamilton | H04W 76/10 709/204 |
| 2014/0188516 A1* | 7/2014 | Kamen | G16H 20/17 705/3 |
| 2015/0005699 A1* | 1/2015 | Burbank | A61M 1/154 604/29 |
| 2017/0143886 A1* | 5/2017 | Wilt | A61M 1/1666 |
| 2018/0043081 A1* | 2/2018 | Lura | A61M 1/1656 |
| 2018/0326138 A1 | 11/2018 | Kalaskar | |
| 2019/0262526 A1* | 8/2019 | Wyeth | A61M 1/1666 |
| 2019/0316948 A1* | 10/2019 | Karol | G01F 22/02 |
| 2020/0121843 A1* | 4/2020 | Wabel | A61M 1/28 |
| 2020/0294392 A1* | 9/2020 | Peesapati | A61M 1/14 |
| 2021/0106228 A1* | 4/2021 | Siedenburg | A61B 5/308 |

FOREIGN PATENT DOCUMENTS

| | | |
|---|---|---|
| EP | 1187642 | 3/2002 |
| EP | 1592494 | 6/2009 |
| EP | 2719406 B1 | 5/2016 |
| EP | 3016695 B1 | 5/2016 |
| EP | 2827916 B1 | 8/2017 |
| EP | 3222305 B1 | 9/2017 |
| EP | 2484333 | 11/2017 |
| EP | 1648536 | 12/2017 |
| EP | 1648536 B1 | 12/2017 |
| EP | 3285825 A1 | 2/2018 |
| EP | 2833938 | 6/2018 |
| EP | 3395382 A1 | 10/2018 |
| EP | 3439712 A1 | 2/2019 |
| WO | 2017193065 A1 | 11/2017 |

OTHER PUBLICATIONS

Response to Extended Search Report dated May 10, 2022, from counterpart European Application No. 20204333.7 filed Nov. 4, 2022, 7 pp.

* cited by examiner

APPARATUS FOR DIALYSIS AND COMMUNICATION METHOD FOR A DIALYSIS MACHINE

FIELD

This invention relates to medical apparatus in particular for dialysis and a communication method for use with such apparatus.

BACKGROUND

One type of dialysis for the treatment of kidney failure is peritoneal dialysis (PD) which uses the lining of a patient's abdomen, the peritoneum, to filter blood while it remains inside the body. Peritoneal Dialysis is an effective way to treat patients with End Stage Renal Disease and acute patients with renal failure. The patient is provided with a catheter that includes a transfer set for selective connection to a dialysis solution or a drain bag. A dialysis solution ('dialysate' or 'peritoneal dialysis fluid') comprising water with other electrolytes is warmed to body temperature and then introduced into the peritoneal cavity of the patient via the catheter. The solution remains here for a period of time required to clean the blood of waste products, toxins and excess fluid and these are then removed from the body to leave the right amounts of electrolytes and nutrients in the blood. The machine or 'cycler' may repeat the exchange process a number of times (cycles), as required for a particular patient.

Conventionally dialysate consists of purified water, glucose and electrolytes, with the concentration of electrolytes resembling that which occurs naturally in the blood. It is prepared according to an individual patient's needs to help regulate their electrolyte and acid-base balance and remove metabolic waste products. The dialysate components are normally shipped in the form of concentrates, with basic and acidic concentrates being prepared separately. The basic concentrate is usually supplied as a dry concentrate consisting of pure sodium bicarbonate which is made up into a saturated solution and the acidic concentrate is usually provided as a liquid concentrate. If it is provided as a dry concentrate, the entire concentrate must be dissolved before being diluted to form the dialysate. This requires a large volume of liquid and multiple components for providing the peritoneal dialysis fluid, increasing the time required for production of the fluid. Concentrate may also be wasted during the production of the correct peritoneal dialysis fluid and difficulties may be encountered in providing the correct concentration of electrolytes in the fluid for a particular patient.

In a newly developed dialysis machine it has been proposed to provide an architecture in which one part of the machine will be used to prepare the dialysate from purified water (purifying a domestic water supply) and the concentrate and another part to cycle the prepared dialysate through the patient via a cannula into the patent's peritoneum.

It will be appreciated that a suitable location for a water supply for generating the dialysate may not be conveniently located relative to the where the dialysis is to be performed. For example, the patient may prefer to rest on a bed in a bedroom and the nearest source of water may be located in a bathroom some meters distant.

A dialysis machine architecture has been proposed for home use or informal non-medical environments in which one part or module is located, for example, in the bathroom to produce the dialysate and the other part or module is located for example, at a bedside for administrating the dialysate to the patient. It has been proposed to provide a communication link utilizing a wireless communication protocol Wi-Fi between the modules or parts to facilitate the communication of data and instructions between the modules.

The present invention arose from a realization by the inventors that in the environment of a patient's home a WI-FI communications link may not be reliable. The reason for this is that a patients' home offers a wide range of differing environmental conditions which will affect the propagation of radio waves.

Radio waves propagate through theoretical free space in a line of sight manner That is to say, the radio waves pass in a straight direct route form the transmitter to the receiver. However, the home environment of a patient will present a far from ideal or indeed predictable environment for propagation. Patients' house will include a wide range of domestic appliances. Some of these will act passively by providing large metallic surfaces which will reflect and scatter radio waves causing multipath propagation in which the receiver receives multiple radio signals in a time dispersed manner For example, a domestic dish washer will provide a radio reflecting surface of approximately 0.5 square meters. It should be realized however that the effect of this in providing a radio reflecting surface will vary as the doors is opened and closed depending upon the location of the radio transmitter. That is to say, the effect on the radio waves in terms of reflection will not be constant. It is complex and changing. Other large radio reflectors may include heating radiators, conventional ovens and microwave ovens.

People moving within the patent's homes may also affect the propagation of the radio waves and within the home there will also be a large number of other radio transmitting devices such as wireless broadband routers, control devices etc. Other devices such as microwave ovens, televisions, washing machines and switches may also add radio interference.

A patients' home is therefore a complex radio propagation environment in which a varying multipath propagation will occur with sporadic or continuous interference from other transmitters.

Accordingly, the patient's home environment has been traditionally viewed as an environment in which Wi-Fi communication in medical equipment has not been possible necessitating equipment to be provided as a single module denying the advantages conferred by a modular approach.

The invention arose in an attempt to mitigate or reduce these issues.

SUMMARY

According to the invention there is provided, medical equipment in particular a dialysis machine comprising two or more modules which modules being operable to provide a first communication link therebetween operable in accordance with a first communications protocol and a second communication link operable in accordance with a second communications protocol and a communications controller configured to determine a quality of the respective communications links such that in the event that one of the communication links offering a quality lower than a threshold the other of the communications link is used for communications.

The invention may be used with a number of different communication protocols. For example, Wi-Fi wireless fidelity, Bluetooth, Zigbee, Z-Wave, 6LoWPAN, NB-IOT etc. Preferably however, where the first protocol is a wireless based protocol the second protocol is one which does not use radio waves to provide the link. For example, the second communications link may be one which uses a physical connection for example by an ethernet cable or an optical wireless transmission and reception. The preferred form of communication link is however one following the POWER-ELINK protocol.

In another aspect the invention provides a method of communicating data between a modules in medical equipment particularly a dialysis machine.

BRIEF DESCRIPTION OF DRAWINGS

A specific embodiment of the invention will now be described with reference to the figures in which.

DETAILED DESCRIPTION

Unless defined otherwise, all technical and scientific terms used generally have the same meaning as commonly understood by one of ordinary skill in the art.

The articles "a" and "an" are used to refer to one or to over one (i.e., to at least one) of the grammatical object of the article. For example, "an element" means one element or over one element.

The term "comprising" includes, but is not limited to, whatever follows the word "comprising." Use of the term indicates the listed elements are required or mandatory but that other elements are optional and may be present.

The term "consisting of" includes and is limited to whatever follows the phrase "consisting of." The phrase indicates the limited elements are required or mandatory and that no other elements may be present.

The term "consisting essentially of" includes whatever follows the term "consisting essentially of" and additional elements, structures, acts or features that do not affect the basic operation of the apparatus, structure or method described.

The term "dialysate" describes a fluid into or out of which solutes from a fluid to be dialyzed diffuse through a membrane. An initial dialysate used for therapy typically contains electrolytes close in concentration to the physiological concentration of electrolytes found in blood. However, the concentration of the dialysate can change over the course of therapy, and can further be adjusted as desired.

The term "dialysis flow path" refers to a fluid pathway or passageway configured to convey a fluid, such as dialysate and/or blood, wherein said pathway forms at least part of, preferably the whole of, a fluid circuit for peritoneal dialysis, haemodialysis, hemofiltration, hemodiafiltration or ultrafiltration. A dialysis machine may be included within the flow path. A dialyzer may be included in the flow path.

The term "mix" means to combine one or more substance so that the resulting mixture is not easily separated. Mixing, especially evenly spreading, of solute and solvent aids and speeds the process of dissolution. Mixing can be achieved by any method, including spraying, stirring, shaking or otherwise agitating. The term "improved mixing" refers to a situation wherein the components of a mixture are more evenly distributed and not clumped together. Improved mixing may be achieved, for example, by speeding the mixing up. In the context of a solution, improved mixing results in a solution of the correct concentration because all or most of the solutes dissolve, rather than remaining as clumps or aggregated within the solvent.

The present invention relates to an improved automated peritoneal dialysis machine that includes a preparator and cycler for in situ preparation of peritoneal dialysis fluid (PDF) for delivery and drainage from a patient with communications links established therebetween.

Figure 1:
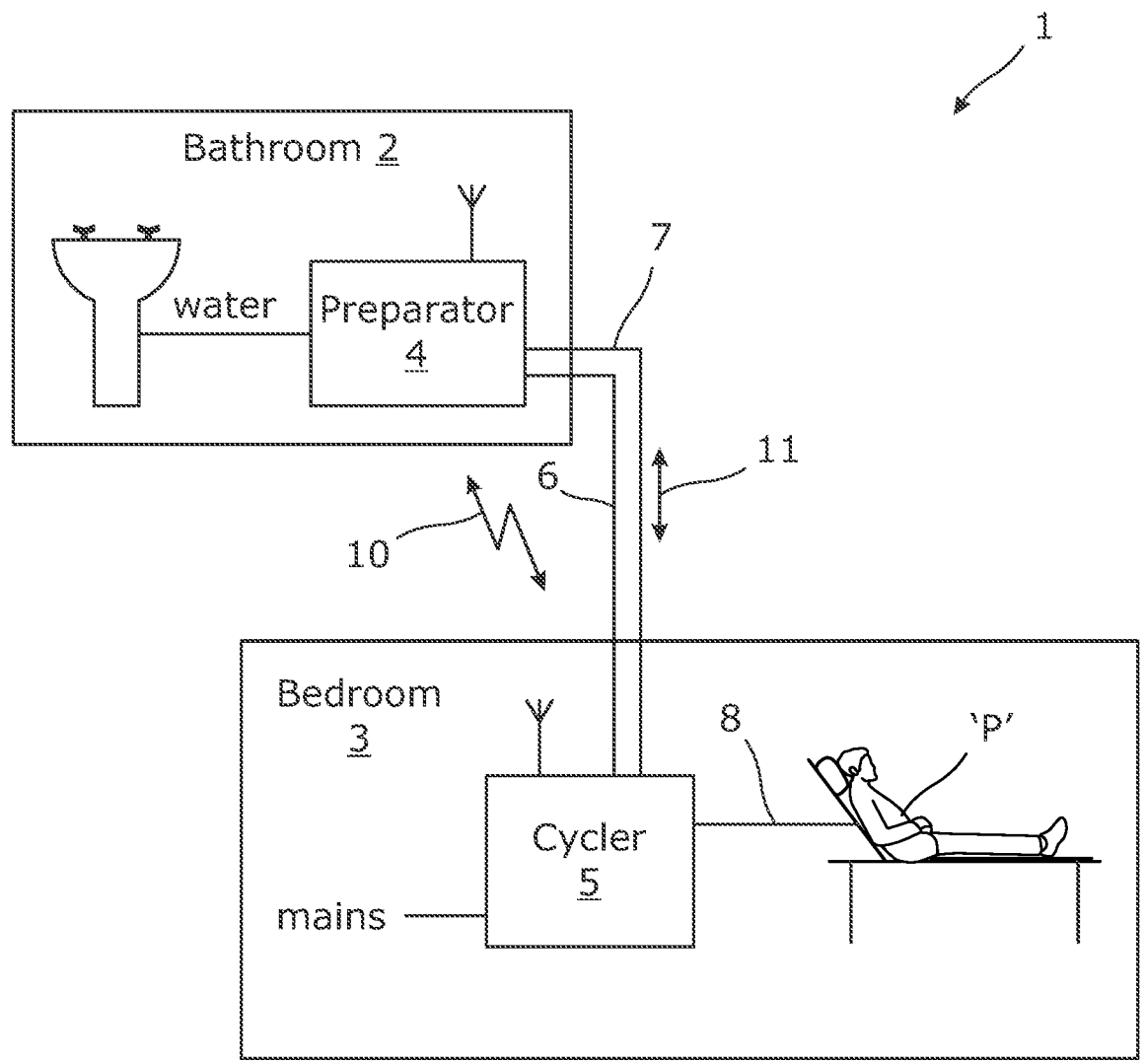
FIG. 1 shows in schematic form a dialysis machine in accordance with an embodiment of the invention in which a preparator module of the machine is located in a patient's bathroom and a cycler module of the machine is located in the patient's bedroom.

FIG. 1 shows an example of a peritoneal dialysis machine 1 according to the present invention. The peritoneal dialysis machine 1 is set up in the patient's home which is represented by two rooms, a bathroom 2 and an adjoining bedroom 3 (although these rooms are representative only and the locations could be other rooms). The peritoneal dialysis machine 1 includes a preparator 4, an automatic cycler 5, a flexible dialysate supply tube 6 and an electrical power supply line 7 which, in this case, is the domestic power supply with each unit being connected to the domestic power socket in each room via a plug (not shown) with a power supply unit which transforms the mains supply voltage down to a suitable voltage.

The preparator 4 is positioned in bathroom 2 as it requires a water source to enable the preparator 4 to generate peritoneal dialysis fluid. The water source may comprise, for example, a tap (faucet) or a more permanent outlet. The preparator 4 first filters the input water and mixes it with a quantity of powered dialysate in accordance with a preprogramed formulation. The powered dialysate will include dextrose, magnesium and calcium and lactate bicarbonate and sodium chloride.

The automatic cycler 5 is positioned in the bedroom 3 where the patient "P" intends to undergo peritoneal dialysis. The cycler 5 is connected to a dialysate delivery tube 8 which is connected to a catheter (not shown) which is inserted into the peritoneum of the patient. The cycler 5 controls the flow of the dialysate into, and out of, the patient in accordance with the required dialysis procedure. Dialysate removed from the patient is stored in a container in the cycler 5 (not shown) for subsequent disposal. This procedure is predetermined and held in memory within the cycler 5 operated under processor control. Broadly, the machine operates by preparing dialysate at the preparator 4, the prepared dialysate is pumped via the dialysate supply tube 6 to the cycler 5. There it is heated to patient temperature and administered to the patent via the delivery tube 8 and the catheter into the patient. After, the appropriate time-period for dialysis, the dialysate is removed from the patient via catheter and the delivery tube 8 and held in storage for subsequent removal and disposal.

As will be appreciated, although the two modules are not collocated, it is necessary for instructions and data to pass between the modules. For example, the preparator 4 will need to provide status updates to the cycler 5 indicating that the dialysate is mixed and available for delivery. The cycler 5 will need to instruct the preparator 4 to commence with delivery, or to increase, or reduce the rate of delivery. Error states may need to be passed. For example, the preparator 4 may experience a problem with the water supply pressure and that will need to be communicated to the cycler and indicated as a fault condition on a display. Accordingly, the preparator 4 and the cycler 5 are each provided with a suitably programmed processor to control its respective functions. In addition, a master processor or controller is provided or designated to control the function of the machine as a whole. These processors (or one processor programmed to provide a number of processing functions) provide in addition a communication function to allow the modules to interoperate and to be controlled.

In this embodiment of the invention, there are two communications links which are operable to enable communications between the modules. A first communications link 10 using radio and operating in accordance with a Wi Fi communications protocol and a physical communications link 11 provided via the domestic power supply 7 over which a Powerlink communications protocol is established and used. Such communications protocols are well known to the person skilled in the art.

Figure 2:
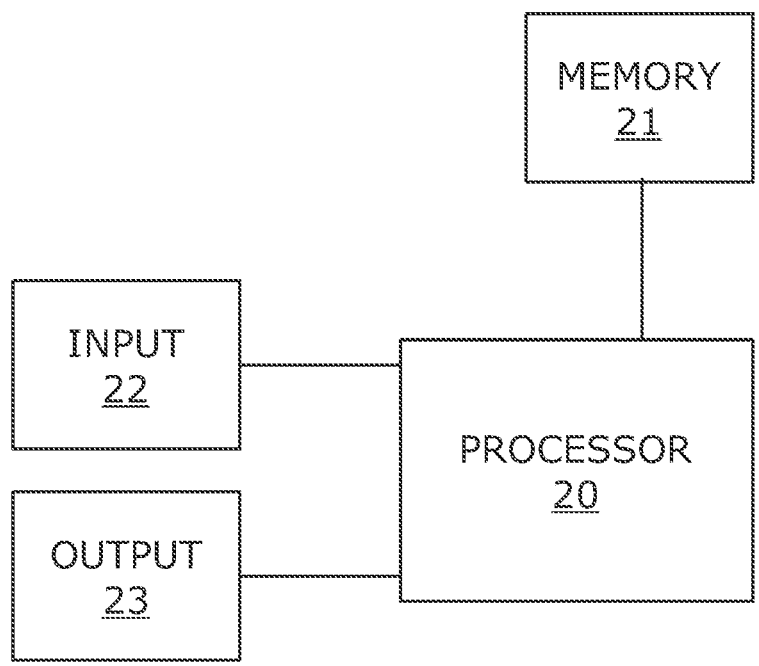
FIG. 2 shows in schematic form the architecture of each of the modules.

FIG. 2 shows the basic architecture of each module. A processor 20 is a microprocessor operating in accordance with software instructions held in a memory 21. These may be held in a variety of forms such as low or high level language instructions which are executed. The processor 20 receives data and signals from input devices 22 and provide data and signals to output device 23. The input device may include, switches, sensors keypads, keyboards touch sensitive screens for example. Example of sensors may be pressure sensors, flow rate sensors, temperature sensors, touch sensors. The touch sensors may allow user input to control the dialysis.

The output devices may include user information devise such as displays, lights or devise responsive to output data or commands For example, heaters, pumps or valves. In particular, the preparator will include a pump controlled in this manner to transfer the dialysate to the cycler.

The processor is programmed to provide a number of different functions. In essence, this may be conveniently thought of as providing different processing functions to provide the full functionality of machine or module. One of the modules will provide a master controller function to govern the operation of the dialysis machine as a whole. In this embodiment the cycler 5 processor becomes the master controller.

The way in which the modules are configured, in accordance with the invention, to cater for communication therebetween will now be described with reference to FIG. 3.

Figure 3:
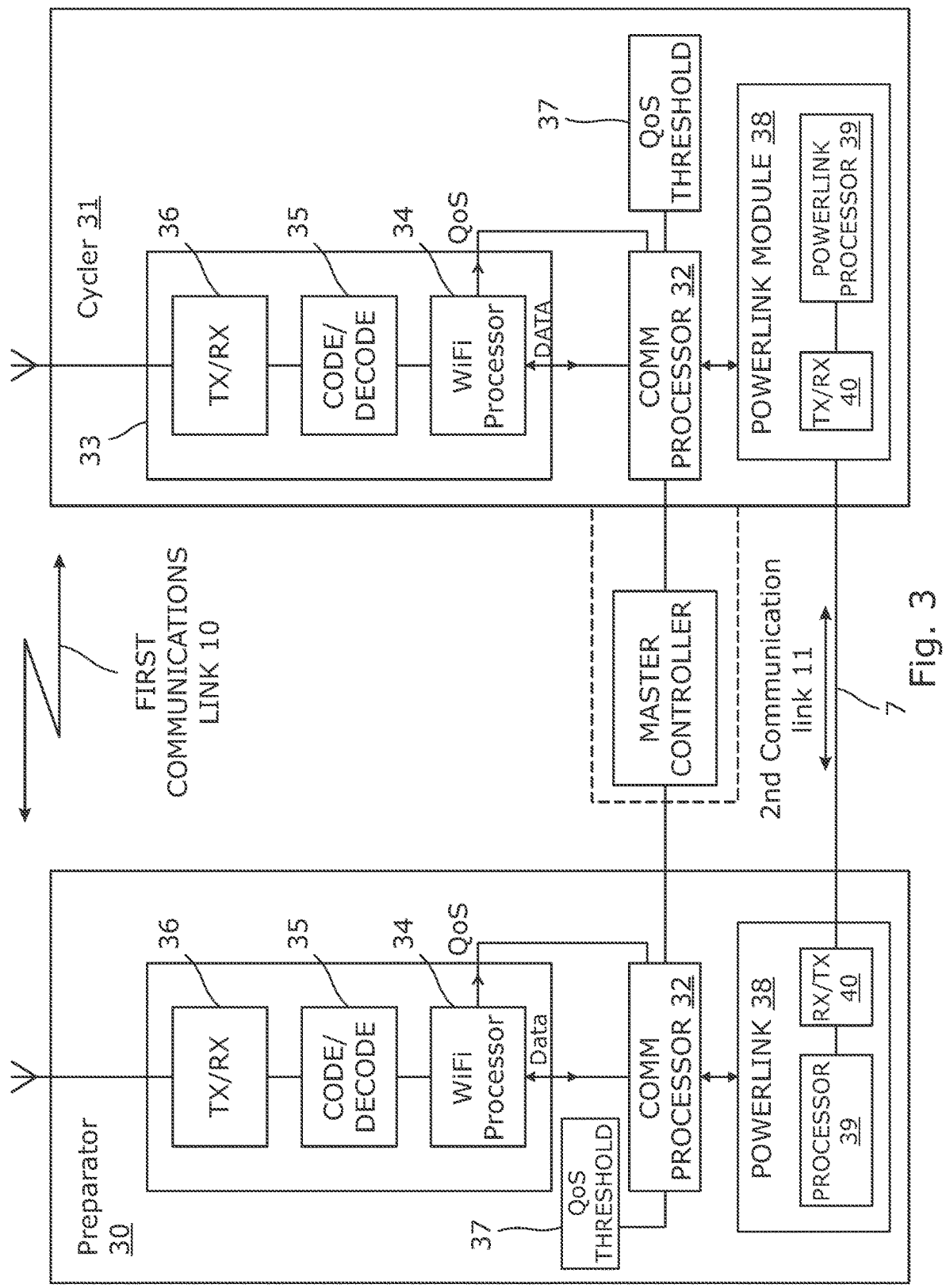
FIG. 3 shows in schematic form the dialysis machine of FIG. 1 showing the blocks of the communication sections of the modules.

As is shown in FIG. 3, the preparator 4 is provided with a communications section 30 and the cycler is provided with a similar communications section 31. As the communications sections are similar only the communications section for the cycler 4 will be described in detail. Like components between the modules are indicated by use of the same reference numbers. Taking the cycler communications section 31, the section is governed by a communications processor 32. This governs the selection and handover between two communications links. The first communications link is supported by a Wi-Fi module 33. This includes a Wi-Fi processor 34, and encoder and decoder section 35, and a transmitting/receiving section 36. The operation of these blocks will be understood by a person skilled in the art of communications protocols.

Significantly, the Wi-Fi processor determines a Quality of Service (QoS) for the communication link 10. As will be understood by persons skilled in the art of communications, QoS is a measure of the data loss or delay in a communications link. When there is a low QoS, data is delayed or lost leading to the communications link being unusable. By comparing a current QoS value held in memory 37 the processor will determine whether or not the Wi-Fi communications link 10 is performing satisfactorily. In the event that it is not, further communications or the ongoing present communication may be passed to the Powerlink communications module 38 for transmission using the second communications link 11 over the domestic wiring 7. A handover protocol will be followed to ensure that data communications data is not lost or the transmission is repeated.

The Powerlink module 38 includes a Powerlink processor 39 controlling a transmitter receiving section 40 which operated in accordance with the Powerlink protocol. This is an Ethernet type protocol but may be a different protocol for communicating over a wired link.

Whatever communications link is used, the data and signals received and decoded by the Wi-Fi communications processor 32 or the Powerlink processor are transmitted to the master controller from the communications processor 32. The master controller then processes the data and interprets the message to control the dialysis machine as a whole. This may involve further communications to be passed by the current preferred or active communication link.

It will be appreciated that at any point in time both communication links may be established and the link offering the better QoS may be selected for communications. This may be on the basis of all of the communications being routed via one link or the greater part of the communications or in some embodiments on the basis of the importance of the data to the performance of the dialysis machine.

It will be appreciated that the invention in its broadest sense allows any two or more communications links to be provided operating in accordance to a mixture of communications protocols. In the described embodiment, two links are provided but three or more communications links may be provided. Both or all links may operate in accordance with different communications protocols or the same. For example, two wireless radio communications links may be provided operating on different frequency bands but both using the Wi-Fi protocol. One communications link may be preferred. For example, in the described embodiment the Wi-Fi link may be the preferred link to which communications may default providing the required QoS is achieved.

In the described embodiment power for the preparator 4 is provide by a wired link to the cycler 5. However, electrical power may be provided by use of a battery at the preparator or via a connection to another power source.

One skilled in the art will understand that various combinations and/or modifications and variations can be made in the described apparatus, methods and uses depending upon the specific needs for operation. Moreover, features illustrated or described as being part of an aspect of the invention may be used in the aspect of the invention, either alone or in combination.

What is claimed is:

1. A dialysis machine, comprising:
   two or more modules, each module of the two or more modules comprising a processor operating in accordance with software instructions held in a non-volatile memory carrier, each module of the two or more modules being operable to provide two or more communications links having a first communications link therebetween operable in accordance with a first communications protocol and a second communications link operable in accordance with a second different communications protocol, and
   a communications controller configured to:
      determine a quality of the respective communications links; and in response to determining that one of the communications links offers a quality lower than a threshold, use any one of the other of the communications link for communication, wherein a first module of the two or more modules comprises a preparator, wherein a second module of the two or more modules comprises a cycler, and wherein the first module is configured to communicate a status update to the second module regarding availability of a dialysate.

2. The dialysis machine of claim 1, wherein at least one of the protocols is a wireless communications protocol.

3. The dialysis machine of claim 2, wherein the wireless communications protocol is a radio communications protocol.

4. The dialysis machine of claim 3, wherein the wireless communications protocol is a Wi-Fi protocol.

5. The dialysis machine of claim 1, wherein at least one of the communications links comprises a wired link.

6. The dialysis machine of claim 5, wherein the communications protocol operates in accordance with a Powerlink protocol.

7. The dialysis machine of claim 1, wherein the second module is configured to provide an instruction to the first module configured to one or more of commence delivery of the dialysate, increase a rate of delivery of the dialysate, or decrease the rate of delivery of the dialysate.

8. The dialysis machine of claim 1, wherein the two or more communications links are operable in accordance with additional communication protocols corresponding to the number of modules.

9. A method of communicating between modules in a dialysis machine comprising:

establishing a first communications link between a first module and a second module of the modules in accordance with a first communications protocol;

establishing a second communications link between the first module and the second module in accordance with a second communications protocol;

determining a quality of the first communications link and or the second communications link;

selecting the first or second communications link for communication between the first module and the second module on the basis of the determined quality; and communicate, by the first module to the second module, a status update regarding availability of the dialysate, wherein the first module comprises a preparator, and wherein the second module comprises a cycler.

10. The method of claim 9, further comprising:

comparing the quality with a threshold value; and in response to determining that the value is less than the threshold, choosing the other of the communications links for communication.

11. The method of claim 9, further comprising:

determining the quality of the first communications link and the quality of the second communications link;

comparing the quality of the first communications link and the quality of the second communications link; and selecting one of the first communications link and the second communications link having a greater quality for communications between the modules.

12. The method of claim 9, wherein the quality of the communications link or links is a Quality of Service (QOS).

13. The method of claim 9, wherein each of the first module and the second module comprises a processor and is configured to provide the first communications link and the second communications link.

14. A non-volatile memory carrier comprising processor executable instructions, the instructions being configured to, when executed, cause at least one processor to:

establish a first communications link between a first module and a second module of a dialysis machine in accordance with a first communications protocol;

establish a second communications link between the first module and the second module in accordance with a second communications protocol;

determine a quality of the first communications link and or the second communications link;

select the first or second communications link for communication between the first module and the second module on the basis of the determined quality; and cause the first module to communicate a status update to the second module regarding availability of the dialysate, wherein the first module comprises a preparator, and wherein the second module comprises a cycler.

* * * * *